United States Patent [19]

Friebe et al.

[11] Patent Number: 6,162,756

[45] Date of Patent: Dec. 19, 2000

[54] TIN CATALYSTS, A PROCESS FOR THEIR PRODUCTION, THEIR USE AND CROSS-LINKABLE MIXTURES CONTAINING THEM

[75] Inventors: Robert Friebe, Leverkusen; Hans Sattlegger, Odenthal; Karl-Heinz Sockel; Wilhelm Weber, both of Leverkusen; Axel Wilms, Bergisch Gladbach, all of Germany

[73] Assignee: GE Bayer Silicones GmbH & Co. KG, Erkrath, Germany

[21] Appl. No.: 09/043,185

[22] PCT Filed: Sep. 12, 1996

[86] PCT No.: PCT/EP96/03838

§ 371 Date: Mar. 12, 1998

§ 102(e) Date: Mar. 12, 1998

[87] PCT Pub. No.: WO97/10271

PCT Pub. Date: Mar. 20, 1997

[30] Foreign Application Priority Data

Sep. 13, 1995 [DE] Germany .......................... 195 33 963

[51] Int. Cl.⁷ ........................ B01J 31/00; C08G 77/06; C08G 77/08

[52] U.S. Cl. ................ 502/155; 502/152; 528/18

[58] Field of Search ............... 528/18; 502/152, 502/155

[56] References Cited

U.S. PATENT DOCUMENTS

| | | | |
|---|---|---|---|
| 3,525,778 | 8/1970 | Lengnick . | |
| 3,773,694 | 11/1973 | Nakata et al. | 502/155 |
| 4,749,766 | 6/1988 | Millet | 528/18 |
| 5,424,383 | 6/1995 | Kimura et al. | 528/12 |
| 5,502,144 | 3/1996 | Kuo et al. | 528/18 |
| 5,534,588 | 7/1996 | Knepper et al. | 524/730 |
| 5,668,194 | 9/1997 | Ando et al. | 523/201 |
| 5,686,546 | 11/1997 | Henderson | 528/12 |
| 5,691,435 | 11/1997 | Herzig et al. | 528/15 |
| 5,698,628 | 12/1997 | Masuda et al. | 524/806 |

*Primary Examiner*—Elizabeth D. Wood
*Attorney, Agent, or Firm*—Norris, McLaughlin & Marcus, P.A.

[57] ABSTRACT

Storage-stable crosslinkable RTV-1 compositions comprising at least one tin catalyst obtained by the reaction of at least one organotin compound with at least one monoorthophosphoric acid or mixture of mono and di-orthophosphoric acids, and at least one crosslinkable polysiloxane.

12 Claims, No Drawings

TIN CATALYSTS, A PROCESS FOR THEIR PRODUCTION, THEIR USE AND CROSS-LINKABLE MIXTURES CONTAINING THEM

The present invention relates to novel tin catalysts, to a process for the production thereof and use thereof and to crosslinkable mixtures containing these novel tin catalysts.

It is generally known to use organotin compounds as catalysts in condensation-crosslinking 1 and 2 component polysiloxane compositions, hereinafter referred to as RTV-1 or RTV-2 (room temperature vulcanising component $\underline{1}$ or $\underline{2}$) compositions, which cure to yield elastomers by the action of water or on absorption of atmospheric humidity.

Diorganyltin compounds, such as dialkyltin dicarboxylates or the reaction products thereof with alkoxysilanes are conventionally used as catalysts in polysiloxane compositions. Examples of such compounds are, inter alia, dibutyltin diacetate, dibutyltin dioctoate, dibutyltin dilaurate, dioctyltin dioctoate, dioctyltin dilaurate or reaction products of dibutyltin oxide with silicic acid esters, such as polymethyl silicate, tetraethoxy silicate and polyethyl silicate.

U.S. Pat. No. 3,525,778 additionally describes organophosphatostannanes of the general formula

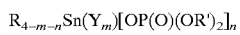

$$R_{4-m-n}Sn(Y_m)[OP(O)(OR')_2]_n$$

in which

Y means a halogen, alkoxy or aryloxy group,

R and R' mean optionally substituted hydrocarbon residues, m means 0, 1 or 2 and n means 1, 2 or 3 and the sum of m+n is 1, 2 or 3, and the use thereof as catalysts in curing polysiloxane compositions. These products are distinguished by elevated activity and result in rapid curing of the polysiloxane compositions.

However, when used in polysiloxane compositions, tin catalysts known from the literature exhibit the disadvantage that they not only have the desired catalytic action on the condensation reaction but they also bring about unwanted polymer degradation reactions. This results, for example, in the loss or a retardation of the crosslinking properties of RTV-1 products. Polymer degradation reactions may also occur in RTV-2 products, in which the catalyst is usually stored in a separate component and mixed with the other component only shortly before use of the product. The consequences of this are, inter alia that the catalyst component, in particular in pasty formulations, is degraded during storage and viscosity falls undesirably or the reactivity changes.

The object of the present invention was to provide tin catalysts which do not exhibit the disadvantages of known products and are suitable as catalysts for RTV-1 or RTV-2 compositions.

It has surprisingly been found that reaction products of organotin compounds with orthophosphoric acid and/or the esters thereof exhibit distinct advantages over the compounds known from the literature. The novel tin catalysts according to the invention are particularly suitable as catalysts for condensation-crosslinking polysiloxane compositions for the production of RTV products having distinctly improved storage stability. The novel catalysts are furthermore distinguished by elevated reactivity.

The present invention accordingly provides novel tin catalysts obtainable by the reaction of a) at least one organotin compound with b) at least one monoorthophosphoric acid ester and/or orthophosphoric acid and c) optionally further phosphoric acid esters, d) optionally an alkoxysilane or two or more alkoxysilanes.

The term organotin compounds a) includes any known prior art compounds.

Preferred organotin compounds a) are mono-, di- and triorganyltin compounds of the general formula (I)

$$R^1_{4-n}SnX_n \qquad (I)$$

where n=1, 2 or 3, preferably n=2, $R^1$=linear or branched $C_1$–$C_{30}$ alkyl, $C_5$–$C_{14}$ cycloalkyl or $C_6$–$C_{14}$ aryl residues and X=halogen, —$OR^1$, —$OC(O)R^1$—OH, —$SR^1$, —$NR^1_2$, —$NHR^1$, —$OSiR^1_3$, —$OSi(OR)^1_3$ and/or compounds of the general formula $R^1_2SnX'$, $R^1_3SnX'_{1/2}$ and/or $R^1SnX'_{3/2}$ where X'=O, S.

The hydrogen atoms of the linear or branched $C_1$–$C_{30}$ alkyl, $C_5$–$C_{14}$ cycloalkyl or $C_6$–$C_{14}$ aryl residues may here also be substituted by halogen atoms, OH, $NH_2$, $NO_2$ or $C_1$–$C_6$ alkyl residues.

In the event that the residues X, X' and $R^1$ occur more than once in the molecule, they may be identical or different.

Particularly preferred compounds are dioctyltin oxide, dibutyltin oxide, dimethyltin dichloride, dibutyltin dichloride, tributyltin chloride, dibutyltin dilaurate, dibutyltin diacetate, dibutyltin maleate, dibutyltin dihexoate, dibutyltin dioctoate, dioctyltin dioctoate, dioctyltin dilaurate, dioctyldibutoxystannane and/or tributylethoxystannane.

For the purposes of the invention, monoorthophosphoric acid esters and/or orthophosphoric acid b) preferably comprise orthophosphoric acid and/or the esters thereof of the following formula (II)

$$O=P(OR^2)_{3-m}(OR^3)_m \qquad (II),$$

where m=2 or 3, preferably 2, $R^2$=linear or branched $C_1$–$C_{30}$ alkyl, acyl, $C_2$–$C_{30}$ alkenyl or alkoxyalkyl, $C_5$–$C_{14}$ cycloalkyl or $C_6$–$C_{14}$ aryl residues or a triorganylsilyl or diorganylalkoxysilyl residue, $R^3$=hydrogen and/or a metal, preferably an alkali or alkaline earth metal, and/or compounds of the formula III

$$[O=P(OR^2)_c(OR^3)_bO_a]^{a-}a\cdot[NH_xR^5_{4-x}]^+ \qquad (III)$$

and x may assume values from 1 to 3 inclusive $R^5$=$C_1$–$C_{30}$ alkyl and $(CH_2)_zSi(OR^6)_3$ where z=1–10, preferably 3, where a+b+c=3, wherein a may assume values from 1 to 3 inclusive, b may assume values from 0 to 2 inclusive and c may assume values from 0 to 2 inclusive, $R^6$=$C_1$–$C_5$ alkyl, $C_2$–$C_6$ alkylalkoxy and/or esters of polyphosphoric acid.

In a preferred embodiment of the invention, the compound is of the formula III

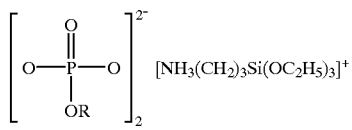

The hydrogen atoms of the linear or branched $C_1$–$C_{30}$ alkyl, acyl, $C_2$–$C_{30}$ alkenyl or alkoxyalkyl, $C_5$–$C_{14}$ cycloalkyl or $C_6$–$C_{14}$ aryl residues may also be substituted here, for example, by halogen atoms, OH, $NH_2$, $NO_2$ or further $C_1$–$C_6$ alkyl groups.

In a preferred embodiment of the present invention, the monoorthophosphoric acid esters contain at least one linear or branched $C_4$–$C_{30}$ alkyl residue as $R^2$. Examples of preferred esters are monobutyl phosphate, monoisodecyl phosphate, mono-(2-ethylhexyl) phosphate, monodecyl phosphate, monohexyl phosphate, monotridecyl phosphate and/or monooctadecyl phosphate. As a result of the production process, the monoorthophosphoric acid esters b) may contain diesters, esters of polyphosphoric acids and/or orthophosphoric acid as contaminants. Orthophosphoric acid alone is less preferred and is preferably used as a mixture with the esters thereof.

In the preferred case where n=2, the tin catalysts according to the invention preferably include the following structural units or compounds:

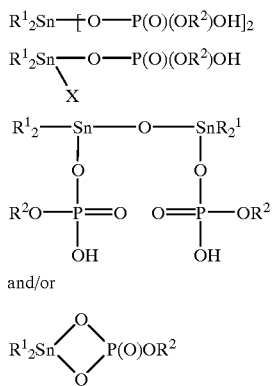

and/or

For the purposes of the invention, phosphoric acid esters c) are preferably di- and triesters of orthophosphoric acid and/or of polyphosphoric acid.

Examples of preferred phosphoric acid esters c) are secondary and tertiary esters of orthophosphoric acid, such as dibutyl phosphate, di-(2-ethylhexyl)phosphate, dihexadecyl phosphate, diisononyl phosphate, di-(trimethylsilyl) phosphate, tributyl phosphate, tri-(2-ethylhexyl)phosphate, trihexadecyl phosphate, triisononyl phosphate and/or tri-(trimethylsilyl)phosphate.

Component c) also includes esters of polyphosphoric acid or mixtures of two or more polyphosphoric acid esters and/or orthophosphoric acid esters. Acidic or neutral salts of ortho- and polyphosphoric acid esters, such as, for example, alkali metal salts, are also suitable.

For the purposes of the invention, alkoxysilanes d) are preferably silicic acid esters, such as, for example, polymethyl silicate, tetramethyl silicate, polyethyl silicate, tetraethyl silicate, tetrapropyl silicate, organyltrialkoxysilanes, such as, for example, vinyltrimethoxysilane, vinyltriethoxysilane, methyltriethoxysilane, methyltrimethoxysilane, vinyltripropoxysilane and vinyltriethoxysilane or the partial hydrolysates thereof.

Methyltrimethoxy-, methyltriethoxy, vinyltrimethoxy and/or vinyltriethoxysilane are particularly preferred in this connection.

The mixtures according to the invention may moreover contain further auxiliary substances.

These auxiliary substances are preferably organic solvents, such as, for example, toluene, hexane, isoparaffins, colouring pigments and/or organic acids, such as, for example, 2-ethylhexanoic acid, benzoic acid, dodecylbenzenesulphonic acid.

For the purposes of the invention, preferred tin catalysts are obtainable by the reaction of 1 mol of at least one organotin compound a), particularly preferably a diorganyltin compound 0.5 to 4 mol, preferably 1 to 3 mol, particularly preferably 1.5 to 2.5 mol of at least one monoorthophosphoric acid ester and/or orthophosphoric acid b), preferably monoorthophosphoric acid 0 to 2 mol, preferably 0 mol, of di- and/or triorthophosphoric acid esters c) and 0 to 5 mol of at least one alkoxysilane d).

Very particularly preferred tin catalysts are obtainable by the reaction of 1 mol of at least one diorganyltin compound a) with 1 to 3 mol of at least one monoorthophosphoric acid ester and 0 to 5 mol of at least one alkoxysilane.

The tin catalysts according to the invention are preferably obtainable by reacting the appropriate tin compounds with the phosphorus compounds at temperatures of between 20 and 200° C., preferably of between 20 and 140° C. In another development of the present invention, the reaction preferably proceeds in a suitable organic solvent. Any inert solvents are suitable for this purpose, such as, for example, aromatic hydrocarbons, such as benzene, toluene, xylene as well as aliphatic, optionally halogenated hydrocarbons, such as, for example, hexane, heptane and tetrachloromethane. The reaction here conventionally proceeds at temperatures of between 20 and 200° C., wherein, if a solvent is used, the reaction temperature is also determined by the boiling point of the solvent.

In another preferred embodiment, the tin catalysts are obtainable by reacting at least one organotin compound a), at least one monoorthophosphoric acid ester and/or orthophosphoric acid b), optionally additionally further phosphoric acid esters c) and optionally one or more alkoxysilanes d) at a temperature of 20 to 140° C.

The present invention also provides a process for the production of the tin catalysts according to the invention, characterised in that a) at least one organotin compound is reacted with b) at least one monoorthophosphoric acid ester and/or orthophosphoric acid and c) optionally further phosphoric acid esters and d) optionally one or more alkoxysilanes.

Further auxiliary substances, such as, for example, organic solvents, such as, for example, toluene, hexane, isoparaffins, colouring pigments and/or organic acids, such as, for example, 2-ethylhexanoic acid, benzoic acid, dodecylbenzenesulphonic acid may also be present during the reaction according to the invention.

This reaction preferably proceeds at temperatures of between 20 and 200° C., preferably of 20 to 140° C.

The present invention furthermore provides the use of the tin catalysts according to the invention as catalysts and stabilisers in polyolefins, polyesters, oils, fatty acids, polyurethanes and polysiloxanes. It is particularly preferred to use the tin catalysts according to the invention as catalysts in crosslinkable RTV-1 and RTV-2 compositions.

When using the catalysts according to the invention in RTV-2 products, it is advantageous to use fillers, such as, for example, highly disperse silicas, paraffins, Vaseline or waxes in order to obtain a pasty presentation. The quantity of auxiliary substances, relative to the total of all constituents a) to d), is highly dependent upon the nature of the constituents used and the concentration thereof and upon the desired consistency of the pasty preparation.

The present invention furthermore provides crosslinkable RTV compositions containing at least one tin catalyst according to the invention, at least one crosslinkable polysiloxane, optionally one or more silane crosslinking agents, optionally fillers and optionally further additives and auxiliary substances.

The RTV compositions according to the invention may in this instance be 1- or 2-component systems. In the 1-component systems, all the constituents are mixed together. 2-Component systems are produced in the form of two separate components and are mixed together only just before use. The crosslinkable polysiloxane is here conventionally stored separately in one component and the silane crosslinking agent and catalyst in the other.

The quantity of the tin catalyst according to the invention is preferably 0.005 to 5 wt. %, preferably from 0.01 to 2.0 wt. %, particularly preferably from 0.1 to 1 wt. %, relative to the total of all components.

For the purposes of the invention, crosslinkable polysiloxanes are polydiorganosiloxanes, preferably polydimethylsiloxanes, wherein the methyl groups are optionally partially substituted by vinyl, phenyl, $C_2$ to $C_8$ alkyl or haloalkyl groups. The polydimethylsiloxanes are preferably substantially linear, but small proportions of organosiloxy units having a crosslinking action may be present. The viscosities of the polymers are preferably between 0.1 and 1000 Pa·s, particularly preferably between 5 and 1000 Pa·s. The crosslinkable polydiorganosiloxane may additionally be partially substituted by unreactive residues, such as, for example, trimethylsiloxy residues.

Preferred reactive residues of the polysiloxanes in RTV-1 compositions are OH groups or trialkyoxysilyl or dialkoxysilyl residues. Preferred trialkoxysilyl or dialkoxysilyl residues are triethoxysilyl and trimethoxysilyl, diethoxymethylsilyl, diethoxyvinylsilyl, dimethoxymethylsilyl or dimethoxyvinylsilyl residues.

In a preferred embodiment of the present invention, the crosslinkable polysiloxane having trialkyoxysilyl or dialkoxysilyl groups as the reactive residues is produced by an appropriate process in the course of the production of the RTV products (cf., for example, DE-A 4 207 212).

The reactive residues of the polysiloxanes in RTV-2 compositions are preferably OH groups.

For the purposes of the invention, silane crosslinking agents are any known prior art silanes having acetoxy, alkoxy, alkoxyalkoxy, aminoxy, amino, amido, acetamido and oximo groups. Examples of these are methyltriacetoxysilane, ethyltriacetoxysilane, methyltrimethoxysilane, methyltriethoxysilane, tetraethyl silicate, vinyltriethoxysilane, vinyltrimethoxysilane, tetrapropyl silicate, methyltris-(methylethylketoximo)silane, methylethoxydi-N-methylbenzamidosilane, methyltris-(butylamino)silane and methyltris-(diethylaminoxy)silane.

The silane crosslinking agent in RTV-2 compositions is preferably at least one alkoxysilane, such as, for example, methyltrimethoxysilane, tetraethyl silicate, vinyltriethoxysilane, vinyltrimethoxysilane, tetrapropyl silicate and/or the partial hydrolysates thereof.

Fillers are preferably reinforcing and non-reinforcing fillers, such as, for example, pyrogenic or precipitated silica, carbon black or silica flour. The fillers may optionally be surface-modified. Mixtures of fillers of any desired composition may also be used. In a preferred embodiment of the invention, the filler is silica.

Additives for the purposes of the invention are preferably plasticisers, coupling agents, pigments, stabilisers, further co-catalysts and fungicides.

In a preferred embodiment of the present invention, the auxiliary substances are silicone plasticisers, such as, for example, polydimethylsiloxanes having trimethylsiloxy end groups and a viscosity of 0.1 to 5 Pa·s, stabilisers, such as, for example, hexamethyldisilazane and/or compounds as are listed in U.S. Pat. No. 4,417,042, coupling agents, such as, for example, organofunctional silanes of the formula (IV):

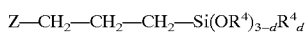

where d=0 or 1,

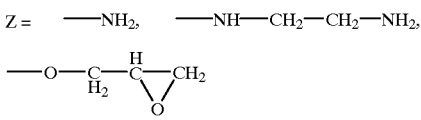

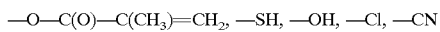

and $R^4$ = a linear or branched $C_1$–$C_{30}$ alkyl residue, and of the formula (V)

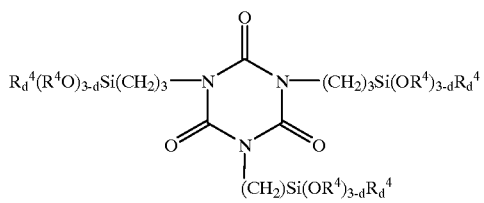

$$R_d^4(R^4O)_{3-d}Si(CH_2)_3\text{—N}\diagdown\text{N—}(CH_2)_3Si(OR^4)_{3-d}R_d^4$$
$$(CH_2)Si(OR^4)_{3-d}R_d^4$$

or urea derivatives.

The hydrogen atoms in $R^4$ may here partially be substituted by halogen atoms, OH, $NH_2$, $NO_2$ or also further $C_1$–$C_6$ alkyl residues.

In a preferred embodiment of the invention, the tin catalyst according to the invention is produced in situ in the crosslinkable RTV composition.

The present invention accordingly provides crosslinked RTV compositions containing at least one tin catalyst, at least one crosslinkable polysiloxane, optionally one or more silane crosslinking agents and optionally further additives and auxiliary substances, characterised in that the tin catalyst is produced in situ during the production of the crosslinkable RTV composition by the reaction of at least one organotin compound a), at least one monoorthophosphoric acid ester and/or orthophosphoric acid b) and optionally further phosphoric acid esters c), one or more alkoxysilanes d) and/or further auxiliary substances e).

The organotin compound is here preferably a reaction product of diorganyltin oxides with silicic acid esters and/or diorganyltin carboxylates, such as, for example, dibutyltin oxide and dioctyltin oxide, dibutyltin diacetate and dioctyltin dioctoate, and component b) is preferably at least one monoester of orthophosphoric acid, such as, for example, monobutyl phosphate, monoisodecyl phosphate, mono-(2-ethylhexyl)phosphate, monodecyl phosphate, monohexyl phosphate, monotridecyl phosphate and monooctadecyl phosphate. Monoisodecyl phosphate, mono-(2-ethylhexyl) phosphate, monodecyl phosphate, monohexyl phosphate, monotridecyl phosphate and/or monooctadecyl phosphate are particularly preferred.

In a preferred embodiment of the present invention, the crosslinkable RTV compositions are of the following composition:

100 parts by weight of at least one crosslinkable polysiloxane,
0.5 to 20 parts by weight of at least one silane crosslinking agent,
0.005 to 5 parts by weight of at least one tin catalyst according to the invention,
0 to 500 parts by weight of at least one filler and
0 to 200 parts by weight of further additives and auxiliary substances.

The additives and auxiliary substances are here preferably of the following composition:

0 to 100 parts by weight of plasticisers,
0 to 20 parts by weight of coupling agents,
0 to 100 parts by weight of pigments,
0 to 20 parts by weight of fungicides and
0 to 20 parts by weight of co-catalysts and stabilisers and
0 to 5 parts by weight of scavengers, wherein the total of all the additives and auxiliary substances in the mixture is greater than 0 and at most 200 parts by weight.

The individual components of the crosslinkable RTV compositions may be mixed together in any desired sequence. It is preferred to mix the components at room temperature. In the case of in situ production of the tin catalyst according to the invention, the individual components are preferably stirred together at room temperature.

The RTV compositions may be produced in any conventional prior art mixing units, such as, for example, planetary mixers, high-speed mixers, butterfly mixers or continuously operated compounding screws.

The following Examples illustrate, but do not limit, the invention.

EXAMPLES

Example 1

150 g of dioctyltin oxide, 87.2 g of mono-2-ethylhexyl phosphate were introduced in 400 g of toluene under a nitrogen atmosphere into a three-necked flask fitted with a stirrer, thermometer, reflux condenser and water separator. The mixture was slowly heated to 125° C. while being stirred and the water formed in the reaction was distilled off and separated in the water separator as an azeotropic mixture with toluene. After approx. 3 hours, the reaction was complete and no further water could be distilled off. The reaction mixture was then evaporated at 80 to 100° C. under a vacuum of 50 mbar down to a residual content of 17 wt. % of toluene. A light yellow, clear liquid was obtained. According to elemental analysis, the product had a tin content of 17.8%.

Example 2

150 g of dioctyltin oxide, 174.4 g of mono-2-ethylhexyl phosphate and 178.7 g of tetrapropyl silicate were introduced under a nitrogen atmosphere into a three-necked flask fitted with a stirrer, thermometer and reflux condenser. The mixture was slowly heated to 160° C. while being stirred and then stirred for a further 3 hours at this temperature. The mixture was then allowed to cool and the reflux condenser replaced with a distillation attachment with a condenser and all the volatile constituents were distilled off within 1 hour under normal pressure at a maximum of 160° C. 73.3 g of distillate were separated, which were identified as propanol by gas chromatography. The reaction product was a yellow, clear liquid having a tin content (according to elemental analysis) of 11.2%.

Example 3

200 g of dioctyltin oxide, 178.3 g of di-2-ethylhexyl phosphate and 64 g of 85% phosphoric acid were introduced in 400 g of toluene under a nitrogen atmosphere into a three-necked flask fitted with a stirrer, thermometer, reflux condenser and water separator. The mixture was slowly heated to 120° C. while being stirred and the water formed in the reaction was distilled off and separated in the water separator as an azeotropic mixture with toluene. After approx. 2 hours, the reaction was complete and no further water could be distilled off. The reaction mixture was then evaporated at a maximum of 110° C., initially at standard pressure and then under a vacuum of 5 mbar down to a residual content of approx. 10 wt. % of toluene. A light yellow, clear liquid was obtained. According to elemental analysis, the product had a tin content of 14.4%.

Comparative Example 4

1368 g of dioctyltin oxide and 1632 g of tetrapropyl silicate were introduced under a nitrogen atmosphere into a three-necked flask fitted with a stirrer, thermometer and reflux condenser. The mixture was slowly heated to 160° C. while being stirred and then stirred for a further 5 hours at this temperature. The reaction product was a yellow, clear liquid. According to elemental analysis, the product had a tin content of 14.5%.

Example 5

70 g of the product produced in Example 4 were reacted at room temperature with 37 g of mono-2-ethylhexyl phosphate. The mixture was a clear, colourless liquid which was used in the RTV-1 compositions for the subsequent tests.

Example 6

100 g of dibutyltin oxide, 168.7 g of di-2-ethylhexyl phosphate were introduced in 300 g of toluene under a nitrogen atmosphere into a three-necked flask fitted with a stirrer, thermometer, reflux condenser and water separator. The mixture was slowly heated to 125° C. while being stirred and the water formed in the reaction was distilled off and separated in the water separator as an azeotropic mixture with toluene within approx. 3 hours. The reaction mixture was then evaporated at 110° C. under a vacuum of 10 mbar down to a residual content of approx. 11 wt. % of toluene. A light yellow, clear liquid was obtained. According to elemental analysis, the product had a tin content of 15.4%.

Comparative Example 7

A solution of dibutyltin dioctoate in 50% toluene was prepared. This tin catalyst was used for purposes of comparison and is a product known and used in the prior art as a catalyst.

General Procedure for the Production and Evaluation of RTV-1 Compositions

The compositions were produced in a 1 liter planetary mixer in accordance with the following Examples. On completion of production, the compositions were transferred into plastic cartridges. Material for the further tests was taken from the sealed cartridges.

The crosslinking behaviour of the polysiloxane compositions was tested on a sheet of glass, to which end the pastes were applied to a thickness of 2 mm on an area of 40×60 mm. After 24 hours, the material was tested to determine whether it was fully cured down to the surface of the glass.

The mechanical properties of the vulcanisates were determined by sheeting out the pastes to a thickness of 2 mm and testing them to DIN 53 504 after 14 days' curing at 23° C. and 50% relative atmospheric humidity. Hardness was tested to DIN 53 505 after 21 days.

The storage stability of the products was evaluated by storing the pastes in a sealed tube at 50° C. or 100° C. The specimens stored at 50° C. were tested for crosslinking at weekly intervals by removing material from the tube. If the specimens crosslinked perfectly after 1 week, the test was deemed to have been passed. Material specimens were taken daily from the specimens stored at 100° C. and tested. If the specimens crosslinked perfectly after 1 day, the test was deemed to have been passed. Testing of storage stability at 50° C. and 100° C. is a conventional sealant test method which allows the storage stability of the products to be estimated in practice within relatively short periods of time.

Examples 8 to 13

55.0 parts by weight of a polydimethylsiloxane having $Si(CH=CH_2)(OCH_3)_2$ end groups, which had a viscosity of 80 Pa·s at 25° C., were mixed with 29.0 parts by weight of a polydimethylsiloxane having $—OSi(CH_3)_3$ end groups, which had a viscosity of 100 mPa·s at 25° C., and 2.5 parts by weight of vinyltrimethoxysilane in a planetary mixer. 9.5 parts by weight of a hydrophobic silica, obtainable from Degussa under the name Aerosil® R 972, were then incorporated into this mixture and the mixture blended to yield a homogeneous paste. 0.8 parts by weight of 3-aminopropyltriethoxysilane were then added to this mixture and the test was completed by adding the quantity of the tin catalyst listed in table 1.

The RTV-1 products of Examples 8 to 13 all cured perfectly after production. The test results may be found in table 1. Example 13 demonstrates that the tin catalyst according to the invention may be produced in situ during production of the sealant.

Examples 14 to 19

55.0 parts by weight of a polydimethylsiloxane having $Si(CH=CH_2)(OCH_3)_2$ end groups, which had a viscosity of 80 Pa·s at 25° C., were mixed with 29.0 parts by weight of a polydimethylsiloxane having $—OSi(CH_3)_3$ end groups, which had a viscosity of 100 mPa·s at 25° C., and 2.5 parts by weight of vinyltrimethoxysilane in a planetary mixer. 9.5 parts by weight of a hydrophobic silica, obtainable from Degussa under the name Aerosil® R 972, were then incorporated into this mixture and the mixture blended to yield a homogeneous paste. 0.8 parts by weight of 3-aminopropyltriethoxysilane were then added to this mixture and the test was completed by adding the quantity of hexamethyldisilazane and stated in table 2 and the quantity of tin catalyst listed therein.

The RTV-1 products all cured perfectly after production. The test results may be found in table 2. Examples 17 to 19 show that a distinct improvement in storage stability is observable as the quantity of stabiliser hexamethyldisilazane rises (from 0.4 parts by weight, Example 18, table 2). When compared with conventional tin catalysts (comparative tests 15, 16), the storage stability of the combinations of the catalysts according to the invention and hexamethyldisilazane is distinctly better.

TABLE 1

Test results for Examples 8 to 13

| Example no. | Tin catalyst | [parts by weight] | Hardness [Shore A] DIN 53505 | Elongation at break [%] DIN 53504 | Tensile stress (100% elongation) [MPa] DIN 53504 | Tear strength [MPa] DIN 53504 | Storage stability at 50° C. [weeks] | Storage stability at 100° C. [days] |
|---|---|---|---|---|---|---|---|---|
| 8[1)] | Example 4 | 0.4 | 19 | 550 | 0.30 | 1.01 | 0 | 0 |
| 9[1)] | Example 7 | 0.4 | 20 | 405 | 0.42 | 1.29 | 4 | 3 |
| 10 | Example 2 | 0.52 | 23 | 495 | 0.41 | 1.52 | 14 | 12 |
| 11 | Example 5 | 0.61 | 23 | 560 | 0.38 | 1.60 | 20 | 15 |
| 12 | Example 6 | 0.34 | 22 | n.d. | — | — | 18 | 13 |
| 13[2)] | Example 4 | 0.6 | 21 | 490 | 0.39 | 1.41 | 22 | 11 |

[1)]Comparative Example
[2)]An additional 0.32 parts by weight of mono-2-ethylhexyl phosphate were incorporated into the batch.
[3)]An additional 0.36 parts by weight of mono-2-ethylhexyl phosphate were incorporated into the batch.
n.d. Not determined.

TABLE 2

Test results for Examples 14 to 19

| Example no. | Tin catalyst | [parts by weight] | Hexamethyl-disilazane [parts by weight] | Hardness [Shore A] DIN 53505 | Elongation at break [%] DIN 53504 | Tensile stress (100% elongation) [MPa] DIN 53504 | Tear strength [MPa] DIN 53504 | Storage stability at 100° C. [days] |
|---|---|---|---|---|---|---|---|---|
| 14[1)] | Example 4 | 0.4 | 1.0 | 20 | 590 | 0.20 | 0.64 | 2 |
| 15[1)] | Example 7 | 0.4 | 1.0 | 20 | 490 | 0.43 | 1.50 | 11 |
| 16 | Example 5 | 0.61 | 1.0 | 20 | 475 | 0.36 | 1.27 | 25[4)] |
| 17 | Example 5 | 0.60 | 0.8 | 19 | 460 | 0.38 | 1.30 | 25 |
| 18 | Example 5 | 0.60 | 0.4 | 21 | 500 | 0.38 | 1.40 | 22 |
| 19 | Example 5 | 0.60 | 0.2 | 21 | 490 | 0.38 | 1.40 | 12 |

[1)]Comparative Example
[4)]The product was still crosslinkable beyond the stated period; test was discontinued.

What is claimed is:

1. Crosslinkable RTV compositions containing at least one tin catalyst obtained by the reaction of
   a) at least one organotin compound with
   b) at least one monoorthophosphoric acid ester or a mixture of at least one monoorthophosphoric acid ester with at least one di-orthophosphoric acid ester, and
   c) optionally further phosphoric acid esters and
   d) optionally an alkoxysilane or two or more alkoxysilanes,
at least one crosslinkable polysiloxane,
optionally one or more alkoxysilane crosslinking agents,
optionally fillers and,
optionally further additives and auxiliary substances.

2. Crosslinkable compositions according to claim 1, wherein the organotin compound is a compound of the formula $$R^1{}_2SnX_2$$

where
   $R^1$ = linear or branched $C_1$–$C_{30}$ alkyl, $C_5$–$C_{14}$ cycloalkyl or $C_6$–$C_{14}$ aryl residues and
   X = halogen, —$OR^1$, —$OC(O)R^1$—OH, —$SR^1$, —$NR^1{}_2$, —$NHR^1$, —$OSiR^1{}_3$, —$OSi(OR)^1{}_3$ or a compound of the general formula $R^1{}_2SnX^1$, $R^1{}_3SnX'{}_{1/2}$, $R^1{}_3SnX'{}_{3/2}$, or a combination thereof, where X'=O,S.

3. Crosslinkable composition according to claim 1, wherein component C) is a di- or triester of orthophosphoric acid or of polyphosphoric acid or a combination thereof.

4. Crosslinkable composition according to claim 1, wherein component d) comprises silicic acid esters, organyltrialkoxysilanes or a partial hydrolysate thereof.

5. Crosslinkable composition according to claim 1, wherein said catalyst further comprises organic solvents, coloring pigments or organic acids as auxiliary substances e).

6. Crosslinkable composition according to claim 1, wherein said catalyst is obtained by the reaction of
   1 mol of at least one diorganyltin compound a) with
   1 to 3 mol of at least one monoorthophosphoric acid ester and
   0 to 5 mol of at least one alkoxysilane.

7. Crosslinkable RTV composition according to claim 1, wherein the alkoxysilane crosslinking agent is methyltrimethoxy-, methyltriethoxy-, vinyltrimethoxy-, vinyltriethoxysilane or a combination thereof.

8. Crosslinkable RTV compositions containing at least one tin catalyst, at least one crosslinkable polysiloxane, optionally one or more alkoxysilane crosslinking agents and optionally further additives and auxiliary substances, wherein the tin catalyst is produced in situ during the production of the crosslinkable RTV composition by the reaction of at least one organotin compound a), at least one monoorthophosphoric acid ester or a mixture of at least one monoorthophosphoric acid ester with at least one di-orthophosphoric acid ester, and optionally further phosphoric acid esters c), one or more alkoxysilanes d), further auxiliary substances e), or a combination thereof.

9. Crosslinkable RTV composition according to claim 1, further comprising silica.

10. Crosslinkable RTV composition according to claim 7, wherein the monoorthophoshoric acid ester b) is monoisodecyl phosphate, mono-(2-ethylhexyl)phosphate, monodecyl phosphate, monohexyl phosphate, monotridecyl phosphate, monooctadecyl phosphate or a combination thereof.

11. An RTV-1 or RTV/-2 composition comprising at least one tin catalyst obtained by the reaction of
   a) at least one organotin compound with
   b) at least one monoorthophosphoric acid ester or a mixture of at least one monoorthophosphoric acid ester with at least one di-orthophosphoric acid ester, and
   c) optionally further phosphoric acid esters and
   d) optionally an alkoxysilane or two or more alkoxysilanes,
at least one crosslinkable polysiloxane.
optionally one or more alkoxysilane crosslinking agents,
optionally fillers and,
optionally further additives and auxiliary substances.

12. Crosslinkable RTV compositions according to claim 1, wherein the monoorthophosphoric acid ester and the di-orthophosphoric acid ester are compounds of the formula $$O=P(OR^2)_{3-m}(OR^3)_m \qquad (II)$$

where m=2 or 3, $R^2$=linear or branched $C_1$–$C_{30}$ alkyl, acyl, $C_2$–$C_{30}$ alkenyl or alkoxyalkyl, $C_6$–$C_{14}$ cycloalkyl or $C_6$–$C_{14}$ aryl residues or a triorganylsilyl or diorganylalkoxysilyl residue, $R^3$=hydrogen, a metal, or compounds of the formula $$[O=P(OR^2)_c(OR^3)_bO_a]^{a-}a \cdot [NH_xR^5_{4-x}]^+ \qquad (III)$$

wherein x is 1 to 3 inclusive, $R^5$=$C_1$–$C_{30}$ alkyl or $(CH_2)_zSi(OR^6)_3$ z=1–10, a+b+c=3, a is from 1 to 3 inclusive, b is from 0 to 2 inclusive and c is from 0 to 2 inclusive, $R^6$=$C_1$–$C_5$ alkyl, $C_2$–$C_6$ alkylalkoxy or esters of polyphosphoric acid.

* * * * *

UNITED STATES PATENT AND TRADEMARK OFFICE
CERTIFICATE OF CORRECTION

PATENT NO.   : 6,162,756
DATED        : December 19, 2000
INVENTOR(S)  : Friebe et al.

It is certified that error appears in the above-identified patent and that said Letters Patent is hereby corrected as shown below:

Column 14,
Line 7, delete "$C_6C_{14}$ cycloalkyl" and substitute -- $C_5C_{14}$ cycloalkyl --

Signed and Sealed this

Tenth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO.    : 6,162,756
DATED         : December 19, 2000
INVENTOR(S)   : Friebe et al.

It is certified that error appears in the above-identified patent and that said Letters Patent is hereby corrected as shown below:

<u>Title page,</u>
Item [56], References Cited, U.S. PATENT DOCUMENTS,
Delete "5,686,546" and substitute -- 5,686,545 --
Delete "5,698,628" and substitute -- 5,698,682 --

Signed and Sealed this

Twenty-ninth Day of April, 2003

JAMES E. ROGAN
*Director of the United States Patent and Trademark Office*